United States Patent
White, deceased et al.

[11] 4,320,118
[45] Mar. 16, 1982

[54] DECA-, UNDECA-, DODECA- AND TRIDECAPEPTIDES WITH THYMIC ACTIVITY

[75] Inventors: Abraham White, deceased, late of Palo Alto, Calif., by Edna White, administrator; John J. Nestor, San Jose, Calif.; Gordon H. Jones; Pamela M. Burton, both of Cupertino, Calif.

[73] Assignee: Syntex (U.S.A.) Inc., Palo Alto, Calif.

[21] Appl. No.: 218,886

[22] Filed: Dec. 22, 1980

[51] Int. Cl.$^3$ .................... A61K 37/00; C07C 103/52
[52] U.S. Cl. .............................. 424/177; 260/112.5 R
[58] Field of Search .................. 260/112.5 R; 424/177

[56] References Cited
U.S. PATENT DOCUMENTS
4,046,877  9/1977  White et al. ................ 261/112.5 R OTHER PUBLICATIONS
Gonzalez et al., Biochem J., 1971, 309–317.
Kustu et al., The J. of Biological Chem., 249, 6976–6983 (1974).

*Primary Examiner*—Delbert R. Phillips
*Attorney, Agent, or Firm*—Kate H. Murashige; Alan M. Krubiner; Tom M. Moran

[57] ABSTRACT

Novel peptides of the formula:

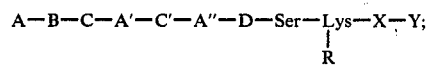

wherein:
A, A' and A'' are each independently Gly, D-Ala, D-Leu, or D-Trp, wherein A may optionally be N-alkylated or N-acylated;
B is Pro, $\Delta^3$-Pro, Thz, or diMeThz;
C and C' are each independently Thr, Ser, Val, or alloThr;
D is Glu, Gln, Asp, or Asn;
R is hydrogen, or is lower alkyl or lower acyl, substituted for one of the hydrogens on the ε-amino group of the lysyl residue;
X is Cys, Ala, ABU, or Cys(Me); and
Y is selected from the group consisting of hydroxy, Pro, Pro-Leu, and Pro-Leu-Met, -NH$_2$, ProNH$_2$, Pro-LeuNH$_2$ and Pro-leu-MetNH$_2$;

and the pharmaceutically acceptable salts thereof, are useful for increasing immunologic competence. Methods for preparation of the peptides are also described.

15 Claims, No Drawings

DECA-, UNDECA-, DODECA- AND TRIDECAPEPTIDES WITH THYMIC ACTIVITY

BACKGROUND OF THE INVENTION

1. Field of the Invention

This invention concerns peptides of short chain length (10, 11, 12 or 13 amino acids) which increase the immunological competence of mammals, especially human beings.

2. Prior Art

A number of substances are known which, when administered to mammals, enhance the ability of the organism's immune system to combat disease. Among these substances are crude extracts of mycobacteria, glycopeptides and modifications of glycopeptides which are derived therefrom, and "thymosins" a family of hormones secreted by the thymus gland. Recently, it has been shown that a fraction of blood, specifically, human serum prealbumin, also possesses such activity (U.S. Pat. No. 4,046,877).

The structure of human serum prealbumin is now clearly established. It is a tetramer of subunits, each of which contains 127 amino acids in the same known sequence (Kauda, Y., et al, *J. Biol Chem.*, 249: 6796 (1974)); and even the three-dimensional configuration has been determined (Blake, C. L. F., et al, *J. Mol. Biol.*, 121(3): 339 (1978). The sequence most relevant to the present invention is that of the N-terminal end, which has been shown to be:

Gly—Pro—Thr—Gly—Thr—Gly—Glu—Ser—Lys—Cys—Pro—Leu—Met
1   2   3   4   5   6   7   8   9   10   11   12   13

A nonapeptide fragment corresponding to the sequence starting at the N-terminal end of each subunit was reported in 1971 as part of earlier efforts to determine the prealbumin structure. (Gonzalez, G. et al, *Biochem. J.*, 125: 309 (1971).

It has now been found, surprisingly, that the deca-, undeca-, dodeca- and tridecapeptides which represent the N-terminal sequence in human serum prealbumin subunits are extremely potent in increasing immunologic competence in mammals. Further, modification of the amino acid sequence of these peptides, at one or more positions by substituting another amino-acyl residue for that normally present, results in a set of peptides with similar or enhanced activity.

SUMMARY OF THE INVENTION

The present invention relates to peptides of the formula:

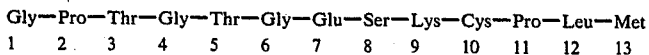

wherein:

A, A' and A" are each independently Gly, D-Ala, D-Leu, or D-Trp; wherein A may optionally be N-alkylated or N-acylated;

B is Pro, $\Delta^3$-Pro, Thz, or diMeThz;

C and C' are each independently Thr, Ser, Val, or alloThr;

D is Glu, Gln, Asp, or Asn;

R is hydrogen or lower alkyl or lower acyl, substituted for one of the hydrogens on the $\epsilon$-amino group of the lysyl residue;

X is Cys; Ala, ABU, or Cys(Me); and

Y is selected from the group consisting of hydroxy, Pro, Pro-Leu, and Pro-Leu-Met, —NH$_2$, ProNH$_2$, Pro-LeuNH$_2$ and Pro-leu-MetNH$_2$;

and to the pharmaceutically acceptable salts thereof. Specifically, these peptides are decapeptides of the formula:

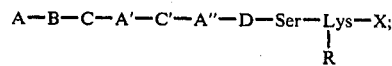

undecapeptides of the formula,

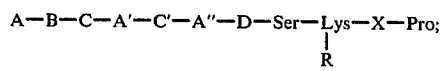

dodecapeptides of the formula,

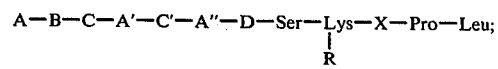

and tridecapeptides of the formula,

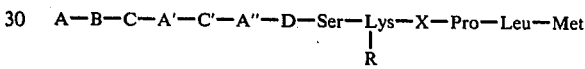

wherein A, A', A"; B; C and C'; D; R; and X are as defined above.

These peptides are useful in increasing immunologic competence of mammals, and, therefore, another aspect of the invention concerns a method for increasing said competence; and still another concerns pharmaceutical compositions appropriate to such a method, containing a peptide as herein described, as the active ingredient.

Still another aspect relates to a process for preparing the compounds of the present invention.

DETAILED DESCRIPTION

Definitions and Abbreviations

As set forth above, and for convenience in describing this invention, the conventional abbreviations for the various common amino acids are used as generally accepted in the peptide art as recommended by the IUPAC-IUB Commission on Biochemical Nomenclature, *Biochemistry*, 11:1726 (1972) and represent L-amino acids, unless otherwise designated, with the exception of the achiral amino acid glycine or other achiral amino acids. All peptide sequences mentioned herein are written according to the generally accepted convention whereby the N-terminal amino acid is on the left and the C-terminal amino acid is on the right.

In addition, the following abbreviations are used for amino acyl residues pertinent to the invention:

| Amino Acyl Residue | Abbreviation |
|---|---|
| $\Delta^3$-L-proline | $\Delta^3$-Pro |

| Amino Acyl Residue | Abbreviation |
| --- | --- |
| thiazolidine-2-carboxylic acid | Thz |
| 5,5-dimethyl thiazolidine-2-carboxylic acid | diMeThz |
| S-methyl-L-cysteine | Cys(Me) |
| α-amino-butyric acid | ABU |
| allo-L-threonine | alloThr |

As above, all abbreviated amino acyl residue represent the L-enantiomer, unless otherwise specified.

As used herein, the term "lower alkyl" refers to a straight or branched chain saturated hydrocarbon group having from 1 to 4 carbon atoms such as, for example, methyl, ethyl, n-propyl, isopropyl, n-butyl, isobutyl, sec-butyl and tert-butyl.

"Lower acyl" refers to

wherein R' is lower alkyl as herein defined.

"N-acylated" refers to an amino group in an amide linkage with lower acyl.

"N-alkylated" refers to an amino group in which one hydrogen has been replaced by lower alkyl.

"N-acylated" is abbreviated NAc, and "n-acylated" amino acid residues have NAc preceding their names or abbreviations. "N-alkylated" is abbreviated NR', and N-alkylated amino acid residues have NR' preceding their names or abbreviations. If the specific alkyl group is designated, the conventional designations, e.g., NMe, NEt, etc., are used in place of NR'. Thus, for example, a glycyl residue which is acylated is abbreviated NAc-Gly; a glycyl which is alkylated is abbreviated NR'-Gly; and a glycyl which has a methyl group substituted at the α-amino is abbreviated NMe-Gly.

In instances where the carboxyl group at the peptide chain is in the form of the amide, NH$_2$ is appended to the abbreviation for the amino acyl residue at this position; e.g., the peptide Gly-Pro-Thr-Gly-Thr-Gly-Glu-Ser-Lys-Ala wherein the alanine at the C terminus is in the form of the amide, is represented by NAc-Gly-Pro-Thr-Gly-Thr-Gly-Glu-Ser-Lys-AlaNH$_2$.

Where no notation is made at the prior to the N-terminal amino acid residue, it is to be understood that H— is attached to the free bond to the nitrogen; where no notation is made subsequent to the C-terminal amino acid residue, it is to be understood that —OH is attached to the terminal carbonyl. Thus, for example, Gly-Gly-Gly means

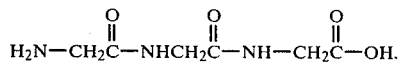

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N, N'-dibenzylethylenediamine or ethylenediamine; or (c) combinations, of (a) and (b); e.g., a zinc tannate salt and the like.

Utility and Administration

The enhancement of immunologic competence may be demonstrated by various indicia utilizing both in vitro and in vivo small animal bioassays well known in the immunology art. For example, the following assays may be mentioned:

azathioprine sensitive rosette assay in vitro or in vivo,
antibody synthesis in vivo or in vitro,
proliferation of lymphoid tissue,
mixed lymphocyte reaction,
blastogenesis with concanavalin A,
in vitro spontaneous rosette assay,
production of cytotoxic lymphocytes,
lymphocyte auto-sensitization in vitro or in vivo.

The above mentioned assays relate to one or more of the general classes of clinical significance for which immunologic competence is believed to be a factor:

stimulation of antibody synthesis,
replacement and restoration therapy,
autoimmune diseases.

The assay of choice for a rapid and accurate indication of activity for increasing immunologic competence is the well-known above mentioned in vitro rosette assay as described by Bach, J. P., *Proc. Natl. Acad. Sci. U.S.A.*, 68: 2734 (1971), wherein the sensitivity of spleen rosette forming cells to azathioprine, [6-(1-methyl-4-nitro-5-imidazolyl)-mercaptopurine] is measured.

A large volume of evidence supports the significance of this assay for assessing immunological status (cf. Bach. J. F., "The Mode of Action of Immunosuppressive Agents", North Holland/American Elsevier Publishing Co., Amsterdam/N.Y., 1975). The peptides of the present invention show activity in this assay at nanogram or picogram levels.

Accordingly, these peptides may be useful clinically for human treatment in situations where immunologic competence is believed to be an important factor, for example, autoimmune diseases, (e.g., lupus erythematosus, ulcerative colitis, autoimmune hemolytic anemia, thyrotoxicosis, rheumatoid arthritis, hepatic circhosis) thymic aplasia and dysplasia, augmentation of immunity in infectious (e.g., bacterial, viral and fungal) disorders, Hodgkin's disease, hypogammaglobulinemic syndrome, aberrant cell proliferative conditions, decrease in immunologic competence due to temporal decline in thymic hormone production, in chemical or radiologically induced immuno-supressed states, and so forth.

The peptides may be made up in the form of conventional pharmaceutical or medicinal preparations by admixture with pharmaceutically acceptable, non-toxic excipients. For example, the material can be mixed with organic or inorganic inert pharmaceutical carriers suitable for parenteral administration, for example, intramuscularly, subcutaneously, or intravenously in the form of, for example, liquid solutions, suspensions, and the like, in unit or divided dosages. Suitable carriers may contain, for example, such common excipients sterile water or saline, polyalkylene glycols such as polyethylene glycol, oils of vegetable origin, hydrogenated naphthalenes and the like.

The pharmaceutical compositions containing the present material may be subjected to conventional pharmaceutical expedients such as sterilization (e.g. by millipore filtration) and can contain conventional pharmaceutical excipients such as preservatives, stabilizing agents, emulsifying agents, bulking binding agents, salts for the adjustment of osmotic pressure, or buffers. The compositions may also contain other therapeutically useful materials, or materials which prolong the duration of action of the present compound. Actual methods of preparing such dosage forms are known or will be apparent to those skilled in the art. An extensive compilation of such formulation techniques may be found, for example, in "Remington's Pharmaceutical Sciences" by E. W. Martin. A preferred formulation is one wherein the peptide is sterilized and lyophilized either solely or with other solid excipients, and stored in a sterile vial until needed. Immediately prior to administration, the desired amount of solvent, e.g. water, water containing preservatives, or a solution of various excipients in water, is added to dissolve the peptide.

In any event, the pharmaceutical composition to be administered will contain a quantity of peptide in a therapeutically effective amount for treatment of the particular condition of concern.

The dosage regimen may consist of unit or divided dosages, but in any event will necessarily be dependent upon the needs of the subject being treated and the judgment of the attending medical practitioner. However, as a broad guideline for most purposes, the peptides will be administered in the range of from about 10 ng/kg/day to about 20 mg/kg/day, preferably from about 100 ng/kg/day to about 5 mg/kg/day. Expressed in alternate terms for an average (70 kg) adult human subject this would be from 700 ng/day to 1.4 g/day preferrably from 7 mg/day to 350 mg/day.

Preferred Embodiments of Peptide Structures

A set of preferred embodiments of the decapeptides, undecapeptides, dodecapeptides, and tridecapeptides of this invention is that wherein A, A' and A'' are each independently Gly, D-Leu, D-Trp or D-Ala, wherein A may optionally be alkylated or acylated at the $\alpha$-amino group; B is Pro, C and C' are Thr; R is hydrogen, D is Glu, Gln, Asp or Asn; and X is Ala, Cys, or Cys(Me).

Especially preferred among these are those embodiments wherein A, A' and A'' are each independently Gly or D-ala and wherein A may optionally be alkylated or acylated at the $\alpha$-amino group; D is Glu or Gln and X is Ala or Cys.

Another preferred set of embodiments is that wherein Y is —OH, —NH$_2$, Pro, or ProNH$_2$.

Synthesis Procedure

The peptides of the present invention may be synthesized by any techniques that are known to those skilled in the peptide art. An excellent summary of the many techniques so available may be found in J. M. Stewart and J. D. Young, *Solid Phase Peptide Synthesis,* W. H. Freeman Co., San Francisco, 1969, and J. Meienhofer, *Hormonal Proteins and Peptides,* Vol. 2, p. 46, Academic Press (New York) 1973 for solid phase peptide synthesis; and E. Schroder and K. Lubke, *The Peptides,* Vol. 1, Academic Press (New York) 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Preferred Synthesis Method

A particularly preferred method of preparing compounds of the present invention involves solid phase peptide synthesis.

In this method the $\alpha$-amino group of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups for amino acids, in general, are t-butyloxycarbonyl (Boc); benzyloxycarbonyl (Cbz); biphenylisopropyloxycarbonyl, 9-fluorenylmethyloxycarbonyl (Fmoc); t-amyloxycarbonyl, isobornyloxycarbonyl, $\alpha,\alpha$-dimethyl-3,5-dimethoxybenzyloxycarbonyl, o-nitrophenylsulfenyl, 2-cyano-t-butyloxycarbonyl, and the like, especially t-butyloxycarbonyl (Boc).

The following are suitable protecting groups for side chain functional groups:

for the Lysine $\epsilon$-amino: Cbz and Boc;
for the serine, threonine and allo-threonine hydroxyls: benzyl (Bz) and tetrahydropyranyl (which form ethers);
for the SH of cysteine: p-methoxy benzyl, benzyl or trityl (which form thioethers), alkyl disulfides, or carbamoyl groups such as ethyl carbamoyl, or acetamidomethyl;
for the carboxyl of glutamic or aspartic acids: benzyl 2,4,6-trimethyl benzyl, or t-butyl to form esters.

The C-terminal amino acid is attached to a suitable solid support. Solid supports useful for the above synthesis are those materials which are inert to the reagents and reaction conditions of the stepwise condensation-deprotection reactions, as well as being insoluble in the media used. Suitable solid supports are benzhydrylamino-polystyrene-divinyl benzene polymer, chloromethylpolystyrene-divinylbenzene polymer, hydroxymethylpolystyrene-divinylbenzene polymer, and the like, especially chloromethylpolystyrene-1% divinylbenzene polymer. For the special case where the C-terminus of the compound will be an amide, a particularly useful support is the benzhydrylamino-polystyrenedivinylbenzene polymer described by P. Rivaille, et al, *Helv. Chim. Acta.*, 54, 2772 (1971).

The attachment to the chloromethylpolystyrene-divinylbenzene type of resin is made by means of the reaction of the $N^\alpha$-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichlormethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage to give a peptide with an acid amide at its C-terminus is effected by treatment with ammonia/alcohol (e.g., methanol or ethanol) solutions at a temperature of about 10°–50°, preferably 25°, for 12–24 hours, preferably 18 hours. (Cleavage to form an ester at the C-terminus followed by aminolysis is an alternative method to give the above product).

The free peptide is cleaved from the resin, with simultaneous removal of the protecting group by treatment with liquid hydrogen fluoride, and anisole at a temperature between about −10° and +10° C., for between about 15 minutes and 1 hour, preferably about 30 minutes.

Side chain protecting groups may be removed by treatment with, for example, anhydrous liquid hydrogen fluoride in the presence of anisole or other carbonium scavenger as described above, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia. In the special case of peptides bound to benzhydryl amino resins, wherein the amide at the C-terminus is desired, deprotection and removal of the peptide from the resin may be effected simultaneously by treatment with liquid hydrogen fluoride and amisole, as above.

The fully deprotected polypeptide is then purified by a sequence of chromatographic steps employing any or all of the following types: ion exchange on a weakly basic resin in the acetate form; hydrophobic adsorption chromatography on underivatized polystyrenedivinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing.

(In those cases where one or more D-amino acids is to be introduced into the peptide, it is often more convenient to employ a racemic mixture of D and L forms than the more expensive resolved D-enantiomer in the synthesis. After introduction at said mixture, a diastereomeric mixture of peptides will result. The diastereomers may be separated using techniques known in the art, and isolated by, for example, the chromatographic procedures described above. However, since the number of diastereomers will increase by a factor of 2 each time a D/L enantiomeric pair is introduced, this separation and isolation should be done at any intermediate state wherein only one D/L mixture has been used, prior to the introduction of the next. Therefore, the separation may simply be done on the final product when only one D/L mixture is used; but when more than one is used in the sequence, intermediate separations will also be necessary.)

Accordingly that aspect of the invention which relates to a process for preparing the peptides herein, concerns a process which comprises:

removing protecting groups and, optionally, covalently bound solid support from a protected peptide to afford a decapeptide, undecapeptide dodecapeptide or tridecapeptide as herein described, or a salt thereof, and (a) optionally, converting the free decapeptide, undecapeptide, dodecapeptide or tridecapeptide to a pharmaceutically acceptable salt, or (b) converting a salt of the decapeptide, undecapeptide, dodecapeptide or tridecapeptide to a pharmaceutically acceptable salt, or (c) decomposing a salt of the decapeptide, undecapeptide, dodecapeptide or tridecapeptide to the corresponding free peptide.

The following examples are given to enable those skilled in the art to more fully understand and practice the present invention. They should not be construed as a limitation upon the scope of the invention, but merely as being illustrative and representative thereof.

PREPARATION A (Preparation of resin bound C-terminal amino acid)

A solution of 3.4 g of Boc-Ala-OH in a mixture of 26 ml of ethanol (EtOH) and 26 ml of $H_2O$ was brought to pH 7 by the addition of a solution of about 2.9 g of cesium carbonate in about 10 ml of water. The solvent was removed at reduced pressure and the residue was resuspended in dry EtOH. The solvent was again removed at reduced pressure and the residue was dried for 24 hours at high vacuum.

The dry residue was suspended in 94 ml of dry dimethylformamide (DMF) and 14.29 g chloromethylpolystyrene-1%-divinylbenzene resin (1.05 mmol Cl/g resin) Merrifield resin—Lab Systems Inc.) was added. The suspension was shaken for 24 hours at 50° C. and then filtered on a glass Buchner funnel. The resin was washed on the filter alternately with DMF/H$_2$O (9:1) and EtOH. After at least 3 washes with each solvent the resin was washed with 3 portions of CH$_2$Cl$_2$ and dried in vacuo to yield 17.05 g Boc-Ala-resin.

EXAMPLE 1

A. In the reaction vessel of a Beckman 990 Peptide Synthesizer was placed 9.524 g (8.38 mmol.) of Boc-L-Ala-resin which is prepared as described in Preparation A, above. Amino acids were added sequentially to this resin by means of a synthesis program, as follows:

| Step | | | |
|---|---|---|---|
| 1 | CH$_2$Cl$_2$ wash | 1 time | 1.5 min |
| 2 | 50% CF$_3$CO$_2$H/CH$_2$Cl$_2$ - deprotection | 1 time | 1.5 min |
| 3 | 50% CF$_3$CO$_2$H/CH$_2$Cl$_2$ - deprotection | 1 time | 30 min |
| 4 | CH$_2$Cl$_2$ wash | 3 times | 1.5 min |
| 5 | 10% triethylamine/CH$_2$Cl$_2$ | 2 times | 1.5 min |
| 6 | CH$_2$Cl$_2$ wash | 3 times | 1.5 min |
| 7 | N$^\alpha$-Boc-amino acid solution | 1 time | add |
| 8 | N,N'-dicyclohexylcarbodiimide solution | 1 time | add |
| 9 | CH$_2$Cl$_2$ rinse and hold - coupling | 1 time | coupling reaction 2 hr |
| 10 | CH$_2$Cl$_2$ - rinse add | 1 time | 1.5 min |
| 11 | CH$_2$Cl$_2$ wash | 3 times | 1.5 min |
| 12 | ethanol wash | 3 times | 1.5 min |
| 13 | CH$_2$Cl$_2$ wash | 3 times | 1.5 min |

Steps 1–13 complete a coupling cycle for one amino acid and completeness of the reaction is checked by the ninhydrin method of E. Kaiser, et al, *Anal. Biochem.*, 34, 595 (1970).

The resin was coupled sequentially with a 2 to 3 molar excess of each protected amino acid and DCC. Thus, the resin was treated during successive coupling cycles with 9.51 g Boc-Lys(Cbz)-OH,
5.13 g Boc-Ser(Bz)-OH,
8.43 g Boc-Glu(OBz)-OH,
4.38 g Boc-Gly-OH,
8.43 g Boc-Thr(Bz)-OH plus 20% for recouple treatment,
4.38 g Boc-Gly-OH,
8.43 g Boc-Thr(Bz)-OH,
5.38 g Boc-Pro-OH,
4.38 g Boc-Gly-OH.

The resin was removed from the reaction vessel, washed with CH$_2$Cl$_2$, and dried in vacuo to yield 17.294 g. of protected polypeptide resin.

The polypeptide product was simultaneously removed from the resin and completely deprotected by treatment with anhydrous liquid HF. A mixture of 10.0 g of protected polypeptide resin and 10 ml of anisole (scavenger) in a Kel-F reaction vessel was treated with about 90 ml of redistilled (from CoF$_3$) anhydrous liquid HF at 0° C. for 45 minutes. The HF was evaporated under vacuum and the residue of the peptide, as its HF salt, was washed with 3×100 ml portions of diethyl ether. The residue was then dissolved in glacial acetic acid, and lyophilized to yield a white powder.

The crude polypeptide was dissolved in water and run through an ion exchange column of Ag3X4A (weakly basic) in the acetate form. The fractions containing product were pooled and lyophilized to yield the crude product in the acetate form, 3.71 g.

Final purification of the peptide was achieved by high performance liquid chromatography on a 5×100 cm column packed with Lichroprep RP18 (reverse phase) support. The sample was loaded in, and the column was eluted with 97% H$_2$O/3% acetonitrile (solution was 0.03 M in NH$_4$OAc, pH 4.5) at 19 ml/min.

The column eluent was monitored by UV absorption at 212 nm and fractions were cut to maximize purity.

The major early eluted peak was pooled and lyophilized from water three times to yield pure Gly-Pro-Thr-Gly-Thr-Gly-Glu-Ser-Lys-Ala, of m.p. 184° (decomposes); $[\alpha]_D^{25} - 70.3°$ (Cl, HOAc);

Amino Acid Analysis: Thr+Ser, 2.5 (3); Gly, 1.0 (1); Pro 1.0 (1); Gly 2.8 (3); Ala 1.1 (1); Lys 1.3 (1).

B. For the synthesis of peptides with a C-terminal amide a benzhydrylamino-polystyrene-divinylbenzene resin is used. The first amino acid is attached to the resin in a reaction vessel using a normal neutralization and coupling sequence as outlined in Preparation A with the addition of one equivalent of hydroxybenzotriazole to the reaction mixture. The coupling is allowed to proceed for 18 hours before checking for completeness. The remainder of the synthesis proceeds as in part A of this Example.

EXAMPLE 2

In a manner analogous to that described in Example 1, other peptides of the present invention have been or are prepared, e.g.

Gly-Pro-Thr-Gly-Thr-Gly-Glu-Ser-Lys-Cys;
m.p. 200° (decomposes)
Amino Acid Analysis: Thr+Ser 2.6 (3); Glu, 1.1 (1); Pro, 1.0 (1); Cys+Cystine 1.0 (1); Gly 2.7 (3); Lys 1.1 (1).

Gly-Pro-Thr-D-Ala-Thr-Gly-Glu-Ser-Lys-Ala;
m.p. 205° (decomposes); $[\alpha]_D^{25} - 51°$ (Cl, HOAc);
Amino Acid Analysis: Thr+Ser, 3.2 (3); Glu, 1.0 (1); Pro 1.1 (1), Gly 2.0 (2), Ala 2.0 (2), Lys 1.1 (1).

Gly-Pro-Thr-Gly-Thr-D-Ala-Glu-Ser-Lys-Ala;
m.p. 225° (decomposes)
Amino Acid Analysis: Thr+Ser 2.6 (3); Glu, 1.0 (1); Pro, 1.0 (1); Gly, 1.9 (2); Ala, 1.9 (2); Lys 1.1 (1).

Gly-Pro-Thr-Gly-Thr-Gly-Glu-Ser-Lys-Cys-Pro
(no data, too small a sample).

Gly-Pro-Thr-Gly-Thr-Gly-Glu-Ser-Lys-Cys(Me),
m.p. 140° (decomposes); $[\alpha]_D^{25} - 49.4°$ (Cl, HOAc);
Amino Acid Analysis: Thr+Ser, 2.5 (3); Glu, 1.1 (1); Pro 1.5 (1), Gly 2.9 (3), Lys 1.0 (1), Cys(Me) 1.3 (1).

NAc-Gly-Pro-Thr-Gly-Thr-D-Ala-Glu-Ser-Lys-Ala,
NAc-Gly-Pro-Thr-Gly-Thr-Gly-Gln-Ser-Lys-AlaNH$_2$,
NAc-Gly-Pro-Thr-D-Ala-Thr-Gly-Glu-Ser-Lys-AlaNH$_2$,
NAc-Gly-Pro-Thr-Gly-Thr-Gly-Glu-Ser-Lys-Ala-Pro,
Gly-Pro-Thr-Gly-Thr-Gly-Glu-Ser-Lys-Ala-Pro,
NAc-D-Ala-Pro-Thr-Gly-Thr-Gly-Glu-Ser-Lys-Ala-Pro-Leu,
Gly-Pro-Thr-Gly-Thr-Gly-Glu-Ser-Lys-Ala-Pro-Leu,
NAc-D-Ala-Pro-Thr-Gly-Thr-D-Ala-Glu-Ser-Lys-Ala-Pro-Leu-Met,
Gly-Pro-Thr-Gly-Thr-Gly-Gln-Ser-Lys-Ala-Pro-Leu-MetNH$_2$.

EXAMPLE 3

Conversion of a Salt to a Pharmaceutically Acceptable salt or other Salt.

A. A solution of 0.1 g of the hydrogen fluoride salt of Gly-Pro-Thr-Gly-Thr-Gly-Glu-Ser-Lys-Ala (See Example 1 purification procedure) is dissolved in 50 ml of water and passed through a column of 50 g Dowex 3 anion exchange resin which had previously been equilibrated with acetic acid and washed with deionized water. The column is eluted with deionized water and the effluent is lyophilized to yield the corresponding acetic acid salt.

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of other compounds of the invention; e.g., those specifically set forth in Example 2.

B. In the case of salts of low water solubility, these may be prepared by precipitation from water utilizing the desired acid. For example: Zinc tannate salt—a solution of 10 mg of Gly-Pro-Thr-Gly-Thr-Gly-Glu-Ser-Lys-Ala acetic acid salt in 0.1 ml of water is treated with a solution of 8 mg of tannic acid in 0.08 ml of 0.25 M NaOH. A solution of 5 mg of $ZnSO_4$ heptahydrate in 0.1 ml of water is immediately added to the solution of the peptide.

The resultant suspension is diluted with 1 ml water and the precipitate was centrifuged. The supernatant is decanted and the residue washed twice with 1 ml portions of water by centrifugation of the precipitate and decantation of the supernatant. The precipitate is dried in vacuo to yield approximately 15 mg of the mixed zinc tannate salt of the above named peptide.

Pamoate salt—to a solution of 10 mg Gly-Pro-Thr-Gly-Thr-Gly-Glu-Ser-Lys-Ala acetic acid salt in a mixture of 1.6 ml of ethanol and 0.1 ml of 0.25 M NaOH was added solution of 11 mg of pamoic acid in 0.3 ml of 0.25 M NaOH. The solvents are removed at reduced pressure and the residue suspended in 2 ml of water, centrifuged, and the supernatant decanted. The precipitate is washed with 1.5 ml $H_2O$, centrifuged, and the supernatant is decanted. The precipitate is dried in vacuo to yield about 10 mg of the pamoate salt of the above named peptide.

In a similar manner other salts of low water solubility may be prepared.

C. Preparation of salt with metal cation; e.g., zinc salt

To a solution of 50 mg Gly-Pro-Thr-Gly-Thr-Gly-Glu-Ser-Lys-Ala acetic acid salt in a mixture of 0.4 ml of 0.25 M NaOH, 0.3 ml water, and 1 ml ethanol is added a solution of 15 mg of $ZnSO_4$ heptahydrate in 0.2 ml of water. The precipitate is centrifuged and the supernatant decanted. The precipitate is washed with 1 ml of water by centrifugation and decantation of the supernatant. The precipitate is dried in vacuo to yield about 50 mg of the zinc salt of the above peptide.

In a similar manner salts with other multivalent cations e.g. calcium, bismuth, barium, magnesium, aluminum, copper, cobalt, nickel, cadmium and the like, may be prepared.

EXAMPLE 4

Preparation of Acid Addition Salt From Free Peptide.

To a solution of 50 mg of Gly-Pro-Thr-Gly-Thr-Gly-Glu-Ser-Lys-Ala as the free base is added 30 ml of 1 N acetic acid. The resulting solution is lyophilized to yield about 50 mg. of the acetic acid salt of the above-named peptide.

Similarly, replacing acetic acid with other acids (in stoichiometrically equivalent amounts relative to peptide) there was obtained other acid addition salts of peptides, for example, the salts with hydrochloric acid, hydrobromic acid, sulfuric acid, phosphoric acid, nitric acid.

EXAMPLE 5

Conversion of Salt to Free Peptide

A solution of 50 mg of Gly-Pro-Thr-Gly-Thr-Gly-Glu-Ser-Lys-Ala acetic acid salt in 25 ml of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield about 50 mg of the corresponding polypeptide as the free base.

Similarly other acid additions salts of peptides of the invention; e.g, those mentioned in Example 2, may be converted to the corresponding free bases.

EXAMPLE 6

Pharmaceutical Compositions

In the compositions illustrated below, Gly-Pro-Thr-Gly-Thr-Gly-Gln-Ser-Lys-Ala$NH_2$ is used as the Active Ingredient. However, other peptides of this invention may, of course, also be used.

| A. | Active Ingredient | 1.0 mg |
| | NaCl | 9.0 mg |
| | Water for injection 9.5 | 1.0 ml. |
| B. | Active Ingredient | 1.0 mg |
| | $NaH_2PO_4$ $H_2O$ | 5.4 mg. |
| | $Na_2HPO_4$ | 8.66 mg. |
| | NaCl | 2.52 mg. |
| | Water for injection 8.5 | 1.0 ml. |
| C. | Active Ingredient | 1.0 mg. |
| | mannitol | 100 mg. |
| | Water for injection 8.5 | 1.0 ml. |
| D. | Active Ingredient | 1.0 mg. |
| | $NaH_2PO_4$ $H_2O$ | 5.4 mg. |
| | $Na_2HPO_4$ | 8.66 mg. |
| | mannitol | 25 mg. |
| | Water for injection 8.5 | 1.0 ml. |

All of the solid ingredients are dissolved in water and lyophilized in a sterile vial. Prior to administering, water is added to dissolve the solids. For vials to be used for multiple dosing, it is preferred that water containing a preservative; e.g., 1.2 mg methyl paraben/ml and 0.12 mg propyl paraben/ml, be used. Reconstituted compositions may be stored at 4° C. for up to two weeks.

We claim:

1. A peptide of the formula:

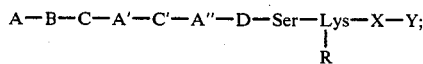

and the pharmaceutically acceptable salts thereof, wherein:
- A, A' and A" are each independently Gly, D-Ala, D-Leu, or D-Trp; wherein A may optionally be N-alkylated or N-acylated;
- B is Pro, $\alpha^3$-Pro, Thz, or diMeThz;
- C and C' are each independently Thr, Ser, Val, or alloThr;
- D is Glu, Gln, Asp, or Asn;
- R is hydrogen, or lower alkyl or lower acyl, substituted for one of the hydrogens on the $\epsilon$-amino group of the lysyl residue;
- X is Cys, Ala, ABU, or Cys(Me); and
- Y is selected from the group consisting of hydroxy, Pro, Pro-Leu, and Pro-Leu-Met; -NH$_2$, ProNH$_2$, Pro-LeuNH$_2$ and Pro-leu-Met-NH$_2$.

2. The peptide of claim 1, and the pharmaceutically acceptable salts thereof, wherein:
- A, A', and A" are each independently Gly, D-ala, D-Leu or D-Trp, wherein A may optionally be N-acylated or N-alkylated;
- B is Pro;
- C and C' are Thr;
- R is hydrogen; and
- X is Ala, Cys, or Cys(Me).

3. The peptide of claim 2, and the pharmaceutically acceptable salts thereof, wherein:
- A, A' and A" are each independently Gly or D-Ala, wherein A may optionally be N-acylated or N-alkylated;
- D is Glu or Gln, and X is Ala or Cys.

4. The peptide of claim 1 and the pharmaceutically acceptable salts thereof, wherein Y is selected from the group consisting of hydroxy, Pro, —NH$_2$, and ProNH$_2$.

5. The peptide of claim 4, and the pharmaceutically acceptable salts thereof, wherein:
- A, A', and A" are each independently Gly, D-ala, D-Leu or D-Trp; wherein A may optionally be N-acylated or N-alkylated;
- B is Pro;
- C and C' are Thr;
- R is hydrogen; and
- X is Ala, Cys, or (Cys(Me)).

6. The peptide of claim 5, and the pharmaceutically acceptable salts thereof, wherein:
- A, A' and A" are each independently Gly or D-Ala wherein A may optionally be N-acylated or N-alkylated;
- D is Glu or Gln; and X is Ala or Cys.

7. The peptide of claim 5 or a pharmaceutically acceptable salt wherein A, A' and A" are Gly, D is Glu, X is Cys(Me) and Y is OH, i.e. Gly-Pro-Thr-Gly-Thr-Gly-Glu-Ser-Lys-Cys(Me).

8. The peptide of claim 6 or a pharmaceutically acceptable salt thereof wherein A, A' and A" are Gly, D is Glu, X is Ala and Y is OH, i.e. Gly-Pro-Thr-Gly-Thr-Gly-Glu-Ser-Lys-Ala.

9. The peptide of claim 6 or a pharmaceutically acceptable salt thereof, wherein A, A' and A" are Gly, D is Glu, X is Cys and Y is OH, i.e. Gly-Pro-Thr-Gly-Thr-Gly-Glu-Ser-Lys-Cys.

10. The peptide of claim 6 or a pharmaceutically acceptable salt thereof, wherein A and A' are Gly, A" is D-Ala, D is Glu, X is Ala and Y is OH, i.e. Gly-Pro-Thr-Gly-Thr-D-Ala-Glu-Ser-Lys-Ala.

11. The peptide of claim 6 or a pharmaceutically acceptable salt thereof, wherein A, A' and A" are Gly, D is Glu, X is Cys and Y is Pro, i.e. Gly-Pro-Thr-Gly-Thr-Gly-Glu-Ser-Lys-Cys-Pro.

12. The peptide of claim 6 or a pharmaceutically acceptable salt thereof, wherein A and A" are Gly, A' is D-Ala, D is Glu, X is Ala, and Y is OH, i.e. Gly-Pro-Thr-D-Ala-Thr-Gly-Glu-Ser-Lys-Ala.

13. A pharmaceutical composition useful for increasing immunologic competence, comprising a therapeutically effective amount of the peptide of claim 1 or a pharmaceutically acceptable salt thereof, in admixture with a pharmaceutically acceptable, non-toxic carrier.

14. A method of increasing immunologic competence in mammals which comprises administering to a subject in need of such treatment, a therapeutically effective amount of, or a pharmaceutical composition containing an effective amount of, the peptide of claim 1 or a pharmaceutically acceptable salt thereof.

15. The peptide of claim 5 or the pharmaceutically acceptable salts thereof; wherein A, A', and A" are Gly, X is Cys(Me), and Y is Pro, i.e. Gly-Pro-Thr-Gly-Thr-Gly-Glu-Ser-Lys-Cys(Me)-Pro.

* * * * *